United States Patent [19]

Clemens

[11] Patent Number: 4,582,913

[45] Date of Patent: Apr. 15, 1986

[54] 5-HALO-4H-1,3-DIOXIN-4-ONE COMPOUNDS

[75] Inventor: Robert J. Clemens, Kingsport, Tenn.

[73] Assignee: Eastman Kodak Company, Rochester, N.Y.

[21] Appl. No.: 619,449

[22] Filed: Jun. 11, 1984

[51] Int. Cl.$^4$ .................. C07D 319/08; C07D 319/06
[52] U.S. Cl. ................................ 549/265; 549/221; 549/274; 560/17; 560/23; 560/43; 560/51; 560/53; 558/87; 558/179
[58] Field of Search .................. 549/274, 265, 221

[56] References Cited

FOREIGN PATENT DOCUMENTS 2149650 4/1973 Fed. Rep. of Germany ...... 549/274
749749 5/1956 United Kingdom ............... 549/274

OTHER PUBLICATIONS

Calvin A. Buehler et al., Survey of Organic Syntheses, vol. 2 (1977) pp. 377–378.
E. V. Dehmlow et al., Liebigs Ann. Chem. (1982), pp. 1753–1755.
Boese, A. B., Ind. Eng. Chem. 32, 16–22 (1940).
Chick et al., J. Am. Chem. Soc. 93, 946–950 (1908).
Chick et al., J. Am. Chem. Soc. 97, 1978–2000 (1910).
Boehme, Org. Syn. Coll., vol. 4, 590–593 (1963).
Blomquist et al., J. Am. Chem. Soc. vol. 70, pp. 29–30 (1948).

Primary Examiner—Norma S. Milestone
Attorney, Agent, or Firm—Clyde L. Tootle; J. Frederick Thomsen

[57] ABSTRACT

Disclosed are novel 5-halo-4H-1,3-dioxin-4-ones and their preparation by treating a compound having the formula

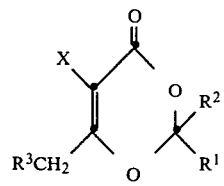

II with $X_2$ or $SO_2X_2$ wherein X is Cl or Br.

3 Claims, No Drawings

5-HALO-4H-1,3-DIOXIN-4-ONE COMPOUNDS

DESCRIPTION

Background of the Invention

This invention relates to novel halogenated 4H-1,3-dioxin-4-one compounds and their preparation and more particularly to 5-halo-4H-1,3-dioxin-4-ones which are useful intermediates for the preparation of α-haloacetoacetic esters.

The preparation of acetoacetic esters by the reaction of alcohols and diketene in the presence of an acid catalyst has been described by A. B. Boese in *Ind. Eng. Chem.* 32, 16 (1940). The sodium enolate salt of ethyl acetoacetate has been reported by Chick et al, *Journal of American Chemical Society* 93, 946 (1908) and 97, 1978 (1910) to be produced by reacting diketene and sodium ethoxide in dry alcohol. The desired α-halogenated product may be obtained by treating the acetoacetic ester with a suitable halogenating agent, e.g. $SO_2Cl_2$. [See Boehme, *Org. Syn. Coll.*, Vol. 4, 590 (1963)].

Reported by Blomquist et al in *Journal of American Chemical Society*, Vol. 70, page 29 (1948) is the preparation of ethyl 2-bromoacetoacetate by first treating ketene dimer in chloroform solution with N-bromosuccinimide followed by reaction with ethyl alcohol. The 2-chloro derivative was similarly prepared by treating ketene dimer with N,2,4-trichloroacetanilide followed by reaction with ethyl alcohol. Reported yields are 43% and 35%, respectively.

A new intermediate compound has now been found which provides an alternate method for producing α-haloacetoacetic esters.

It has been found that by reacting a halogenating agent (i.e., $X_2$ or $SO_2X_2$ wherein X is Cl or Br) with a 4H-1,3-dioxin-4-one compound the monohalogenated derivative, 5-halo-4H-1,3-dioxin-4-one, is obtained.

The 5-halo-4H-1,3-dioxin-4-ones of this invention are obtained in a relatively short reaction time and excellent yield. The unpurified product, for many uses, need not be purified before using in subsequent reactions. In addition, halogenation is achieved without the use of expensive halogenating agents. Moreover, the preparation of α-haloacetoacetic esters using these novel compounds is advantageous for halogen sensitive alcohols since the halogen moiety is introduced prior to opening of the dioxinone ring.

SUMMARY OF THE INVENTION

The present invention relates to novel 5-halo-4H-1,3-dioxin-4-one compounds and to a process for their preparation. The novel compounds of this invention have the formula

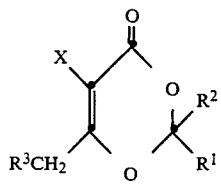
II and are produced by treating a compound having the formula

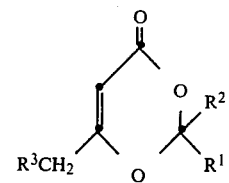
I with $X_2$ or $SO_2X_2$ and recovering the product resulting therefrom. In the above formulae X is Cl or Br; $R^1$ and $R^2$ are each independently alkyl, aryl, substituted aryl, or collectively alkylene; $R^3$ is hydrogen, Cl, Br, alkyl, alkoxy, aryl, substituted aryl, or a hetero moiety.

DETAILED DESCRIPTION OF THE INVENTION

The invention described herein relates to novel 5-halo-4H-1,3-dioxin-4-one compounds and their preparation.

$R^1$ and $R^2$ of the above formulae, are residues of the aliphatic or cycloaliphatic ketone from which the 4H-1,3-dioxin-4-one compounds are derived. The alkyl moieties of the disclosed substituents for $R^1$ and $R^2$ generally can be lower alkyl (i.e., $C_1$–$C_6$), either branched or straight chain. Examples of these include methyl, ethyl, propyl and isobutyl. The aryl substituent generally can be phenyl and the substituted aryl group may contain any substituent which is not reactive with the halogenating agent or does not otherwise interfere with the course of the reaction. Examples of substituted aryl groups include p-nitrophenyl and o-chlorophenyl. Examples of the alkylene groups are tetramethylene and pentamethylene [i.e., —$CH_2(CH_2)_2CH_2$— and —$CH_2(CH_2)_3CH_2$—]. Most commonly and preferably $R^1$ and $R^2$ are each methyl.

$R^3$ of the above formulae may be straight or branched chain alkyl of about $C_1$–$C_{20}$. The alkyl moiety of the alkoxy substituent generally can have 1–4 carbon atoms. Examples of the alkoxy substituent include methoxy and ethoxy. The aryl substituent generally is intended to mean phenyl; substituted aryl is intended to mean p-nitrophenyl. Examples of the heteromoieties include phenylthio, anilino and diethyl phosphonato [i.e., $(CH_3CH_2)_2PO$].

The starting materials as shown by formula (I) are known in the art and/or are readily obtained by methods known to one skilled in the art. [For example, see Boeckman, *Journ. Org. Chem.* 47, 2823–2824 (1982); Blomquist, *Journ. Amer. Chem. Soc.* 70, 29–30 (1948)].

Preparation of the novel 5-halo compounds of formula II is by treating a 1,3-dioxin-4-one of the formula

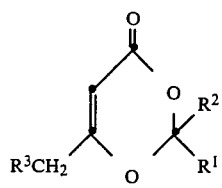
I with $X_2$ or $SO_2X_2$, wherein X is Cl or Br. Elemental chlorine or bromine are the preferred halogenating agents. The conditions of the reaction may be varied considerably, depending on the halogenating agent used and whether the reaction is carried out in a gaseous or liquid phase. In carrying out the reaction, for example, using elemental chlorine or bromine and in a liquid phase the reaction is carried out at temperatures and pressure sufficient to maintain chlorine or bromine in liquid form, i.e. at atmospheric pressure the temperature for chlorine will be below −35° C. and below 59° C. for bromine. Of course, higher temperatures may be used with the use of elevated pressures. It was unexpected that halogenation in this manner would give monohalogenation at the 5-position of the dioxinone ring.

In carrying out the reaction in a liquid phase a solvent is not required but one may be used if desired. Typical solvents which may be used are, for example, aliphatic or aromatic hydrocarbons, or chlorinated aliphatic or aromatic hydrocarbons, including, for example, methylene chloride, chloroform, benzene, chlorobenzene and the like. The amount of solvent generally will be dictated by economy and convenience. A by-product of the halogenation reaction is a hydrogen halide. This by-product generally may be removed by addition of a base to the product mixture such as an amine or carbonate salt, including, for example, pyridine triethylamine, or sodium carbonate.

The halogenating agent will generally be employed in stoichiometric amounts and preferably in slight excess, up to about 1.2 moles per mole of (I). Advantageously, monohalogenation of (I) is achieved rapidly, giving 5-halo-4H-1,3-dioxin-4-ones in excellent yield and of sufficient purity as not to require purification prior to the use thereof in subsequent reactions. Of course, when $R^3$ is Cl or Br the dihalogenated compound will be the resulting product. When a product of even higher purity is desired the crude 5-halo-4H-1,3-dioxin-4-ones may be purified, for example, by column chromatography or distillation with wiped-film evaporation.

The 5-halo-4H-1,3-dioxin-4-ones of this invention are useful intermediates in the preparation of α-haloacetoacetic esters. Depending on the acetoacetic ester desired, these novel compounds may be reacted with a phenol compound or an alkali metal alkoxide to obtain α-haloacetoacetic esters of the formula

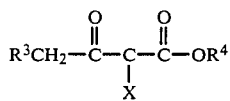

III

In the above formula X is Cl or Br, $R^4$ is the residue of the phenol reactant or the alkali metal alkoxide reactant, and $R^3$ is as previously defined.

The phenol reactant and the alkali metal alkoxide reactant may be represented by the formula $R^4OM$ wherein $R^4$ is alkyl or aryl and M is an alkali metal ion when $R^4$ is alkyl or M is hydrogen when $R^4$ is aryl. For purposes of economy, the alkali metal ion ordinarily will be sodium.

The mole ratio of compound (III) to compound (II) generally may be in the range of at least about 1.0 up to about 2.0 with best results being obtained with a mole ratio of about 1.0 to about 1.2.

The temperatures at which the reaction can be carried out will depend on the particular acetoacetic ester prepared, i.e. depending in part on whether compound (III) is a phenol or an alkali metal alkoxide. Temperatures in the range of about −40° to about 50° C. and preferably ambient temperatures, i.e. 0°-25° C., will generally be used with an alkali metal alkoxide. With a phenol compound, the reaction temperature may range from about 100° to about 200° C. and preferably about 120° to about 145° C. Thus, the range of temperatures at which the α-haloacetoacetic esters can be prepared can vary from about −40° C. up to about 200° C.

A solvent may be used in preparing the α-haloacetoacetic esters if desired. When an alkali metal alkoxide is used the solvent desirably is an alkanol having the same number of carbon atoms as the alkoxide reactant. When compound (III) is a phenol the solvent can be, for example, toluene, xylene, and the like. The amount of solvent is not critical to the reaction and generally will be dictated by economy and convenience.

The following examples are given to further illustrate the invention, but it is to be understood that the invention is not to be limited in any way by the details described therein.

EXAMPLE 1

Preparation of 5-Bromo-2,2,6-Trimethyl-4H-1,3-Dioxin-4-One

Bromine (0.105 mol, 5.38 ml) was added dropwise to a 20° C. solution of 2,2,6-trimethyl-4H-1,3-dioxin-4-one (TKD, 0.1 mol, 14.2 g) in 100 ml $CH_2Cl_2$ over five minutes. The reaction solution was rapidly decolorized and hydrogen bromide evolved. After 15 minutes, the solvent was removed in vacuo to provide 22 g (99%, >95% pure by NMR) of a pale yellow oil which solidified upon refrigeration. Flash chromatography (10% ether/hexane on silica) afforded 16.5 g (75%) of the title compound as colorless plates.

EXAMPLE 2

Preparation of 5-Chloro-2,2,6-Trimethyl-1,3-Dioxin-4-One

A solution of 2,2,6-trimethyl-1,3-dioxin-4-one (0.2 mol, 28.4 g) in 100 ml of $CH_2Cl_2$ was cooled to −50° C. and liquid chlorine (0.25 mol) was added dropwise over five minutes. The solution was allowed to warm to 20° C. over 30 minutes, and the solvent was then removed in vacuo, leaving 35.8 g (100% yield, 92% assay) of a pale yellow oil. A portion of this mixture was purified by flash chromatography (10% $Et_2O$/hexanes on silica) to provide the title compound as white crystals.

EXAMPLE 3

Preparation of 4-Nitrophenyl 2-Chloroacetoacetate

A solution of 5-chloro-2,2,6-trimethyl-4H-1,3-dioxin-4-one (8.8 g, 50 mmol) and 4-nitrophenol (7.65 g, 55 mmol) in 5 ml of xylene under continuous nitrogen purge was immersed in an oil bath preheated to 110° C. The reaction was then heated to 135° C. and then stirred an additional 15 minutes. The pale brown reaction was cooled to 20° C. and the precipitated product washed with ether/hexanes to afford 10.9 g (84%) of the title compound as flaky, white crystals.

EXAMPLE 4

Preparation of Methyl-α-Chloroacetoacetate

A solution of 25% sodium methoxide in methanol (5 ml, 21.6 mmol) was added to a solution of 5-chloro-2,2,6-trimethyl-4H-1,3-dioxin-4-one (3.24 g, 18.4 mmol) in 10 ml of methanol at 20° C. The resulting yellow solution was stirred for 10 minutes, acidified with 10% HCl, and extracted with ether. Evaporation of the ether provided 2.35 g (94% yield, NMR assay ~90%) of a pale yellow oil, which was distilled to provide 1.8 g (66%) of pure title compound as a colorless liquid.

EXAMPLE 5

Preparation of Ethyl-α-Chloroacetoacetate

Sodium metal (0.3 g, 12 mmol) was added to 10 ml of ethanol, and then 5-chloro-2,2,6-trimethyl-4H-1,3-dioxin-4-one (1.76 g, 10 mmol) was added. The reaction was stirred one hour at 20° C., during which time the sodium dissolved. The reaction partitioned between ether and saturated ammonium chloride which had been acidified to pH ~2 with HCl. Evaporation of the ethereal layer, followed by distillation afforded 1.15 g (70%) of the title compound as a colorless liquid.

EXAMPLE 6

Preparation of Ethyl-α-Bromoacetoacetate

Sodium metal (13.7 g, 0.59 mol) was dissolved in 500 ml of absolute ethanol, and the resulting ethoxide solution was cooled to 0° C. Crude 5-bromo-2,2,6-trimethyl-4H-1,3-dioxin-4-one (115.5 g, 0.5 mole at 95% purity) was then added, dropwise, to the chilled ethoxide solution over 30 minutes and the dark orange reaction mixture was stirred an additional 30 minutes at 0° C. The reaction was poured into 500 ml of ether and 550 ml of 1N HCl, and the organic layer was washed repeatedly with water (4×250 ml) and then dried over $Na_2SO_4$. Removal of solvent in vacuo (30° C., 2 Torr), followed by distillation on a 2-inch wiped-film molecular still (120° C. jacket, 0.2 Torr) afforded 68.7 g (71%) of a pale yellow oil (98% pure by gc).

The invention has been described in detail with particular reference to preferred embodiments thereof, but it will be understood that variations and modifications can be effected within the spirit and scope of the invention.

I claim:

1. A compound having the formula

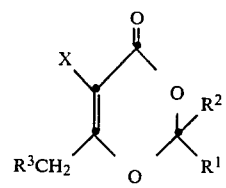

wherein X is Cl or Br; $R^1$ and $R^2$ are each independently lower alkyl having 1 to 6 carbon atoms; phenyl, p-nitrophenyl and o-chlorophenyl or collectively an alkylene selected from the group consisting of tetramethylene and pentamethylene; and $R^3$ is hydrogen, Cl, Br, an alkyl having 1 to 20 carbon atoms, an alkoxy having 1 to 4 carbon atoms, phenyl, p-nitrophenyl, phenylthio, anilino, or diethylphosphonato.

2. The compound of claim 1 wherein X is Cl or Br; $R^1$ and $R^2$ are each methyl or collectively tetramethylene or pentamethylene; and $R^3$ is hydrogen, Cl or Br.

3. The compound of claim 1 wherein X is Cl or Br; $R^1$ and $R^2$ are each methyl; and $R^3$ is hydrogen.

* * * * *